United States Patent [19]

Biollaz et al.

[11] 4,092,310
[45] May 30, 1978

[54] DIFLUOROSTEROIDS AND PROCESSES FOR THEIR MANUFACTURE

[75] Inventors: Michel Biollaz, Basel; Jaroslav Kalvoda, Binningen, both of Switzerland

[73] Assignee: Ciba-Geigy Corporation, Ardsley, N.Y.

[21] Appl. No.: 598,300

[22] Filed: Jul. 23, 1975

[30] Foreign Application Priority Data

Jul. 30, 1974   Switzerland ............... 10478/74

[51] Int. Cl.² .............................. C07J 17/00
[52] U.S. Cl. .................. 260/239.55 D; 260/239.55 C; 260/397.3; 260/397.4; 260/397.45; 260/397.47; 260/397.5
[58] Field of Search ............... 260/397.45, 239.55

[56] References Cited

U.S. PATENT DOCUMENTS 3,318,922   5/1967   Windholz et al. .............. 260/397.4
3,914,265  10/1975   Middleton ..................... 260/397.3

OTHER PUBLICATIONS

"Steroid Reactions" by Dyerassi, (1963), pp. 171–173.
Hasek et al., "Journ. American Chem. Soc.", vol. 82, (1960), pp. 543–548.

*Primary Examiner*—Elbert L. Roberts

*Attorney, Agent, or Firm*—Theodor O. Groeger

[57] ABSTRACT

A novel group of 18,18-difluorosteroids of the general formula

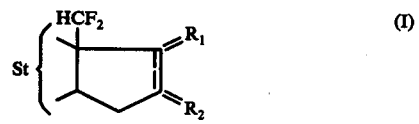

wherein St, $R_1$ and $R_2$ have the meanings given hereinafter is produced by a chemically novel process characterized in that a corresponding 18-oxo compound is treated with a compound of the formula $F_3SX$, wherein X denotes a fluorine atom or an amino group derived from a secondary amine. The compounds of the invention are useful as pharmaceutical intermediates. A number of them are physiologically active and possess hormone-like properties, e.g. those of sexual and/or adrenocortical hormones, such as the gonadotropin-blocking, ovulation-blocking, androgenic, oestrogenic, progestagenic, anabolic, antioestrogenic, antiandrogenic, mineralocorticoid, glucocorticoid and antiinflammatory activity, and can be used in lieu of known hormones or agents possessing corresponding hormone-like properties.

10 Claims, No Drawings

DIFLUOROSTEROIDS AND PROCESSES FOR THEIR MANUFACTURE

The present invention relates to a hitherto unknown group of compounds, the 18,18-difluorosteroids, and to processes for their manufacture. In particular, the invention relates to the compounds of the general formula I

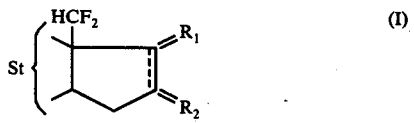

wherein St represents the remaining, optionally substituted and/or otherwise modified, part of the steroid skeleton, $R_1$ denotes an optionally ketalised oxo group, an optionally substituted lower alkylidene radical or an optionally etherified or esterified hydroxyl group conjointly with a hydrogen atom, a cyano group or an optionally substituted lower aliphatic hydrocarbon radical, or denotes a hydrogen atom conjointly with a cyano group or an optionally substituted lower alkyl radical, and $R_2$ denotes a lower alkylidene radical, an optionally etherified or esterified hydroxyl group conjointly with a hydrogen atom, a lower alkyl radical conjointly with a hydrogen atom, or, in particular, denotes two hydrogen atoms, it being possible for a 16,17-double bond to be present in place of one of the said hydrogen atoms of each of the radicals $R_1$ and $R_2$, and to processes for the manufacture of these compounds.

The compounds according to the invention are, above all, derivatives of the naturally occurring D-series, but they can also be present as derivatives of the L-series, which is accessible by total synthesis, or as racemic mixtures of the two antipodes.

Wherever it is used in connection with an organic radical, the term "lower" designates a corresponding radical with at most 7, but preferably with 1 to 4, carbon atoms.

The radical St consists of rings A and B (carbon atoms C-1 to C-10) and the remaining carbon atoms of ring C (C-11 and C-12) and can also carry the angular methyl group (C-19) in the 10-position. It can also be modified in other ways, for example it can possess a structure with expanded or contracted rings, such as the A-nor structure or the A-nor-B-homo structure, and/or can exhibit bridging of the ring, for example the 3α,5-cyclo linkage. The rings A, B and C can take up various configurations with respect to one another, such as, for example, the 5α,9β,10α configuration or the 5β,9β,10α configuration, but above all the 5α,9α,10β configuration or the 5β,9α,10β configuration. The radical St can have one, two or more double bonds, such as in the 1,2-2,3-, 3,4-, 5,10-, 6,7-, 9,10-, 9,11- or 11,12-positions, but above all in the 4,5- or 5,6-positions, it being possible, in the absence of a substituent in the 10-position, for three such double bonds to form an aromatic system, especially in ring A. The radical St can also be substituted by free, etherified and, in particular, esterified hydroxyl groups, for example in the 3-, 11- and/or 19-positions, above all in the 3β- and/or 11β-positions, by free or ketalised oxo groups, especially in the 3- and/or 11-positions, by lower alkyl radicals, for example in the 7α- or especially the 6α-positions, or by halogen atoms, such as bromine or especially chlorine or fluorine atoms, especially in the 2- or, above all, in the 6α- and/or 9α-positions.

A lower alkyl radical is, for example, a n-propyl, i-propyl, n-butyl, i-butyl, sec.-butyl or tert.-butyl radical or a branched or preferably straight-chain pentyl, hexyl or heptyl radical, but above all an ethyl or methyl radical. A lower aliphatic hydrocarbon radical is to be regarded as a lower alkyl radical, for example one of those already mentioned, or an analogous radical which in addition contains one or two multiple bonds, that is to say double bonds or acetylenic bonds, such as, for example, a lower alkenyl, lower alkinyl and allenyl radical, for example a vinyl, allyl, methallyl, propargyl, hexadiinyl and, above all, ethinyl radical. A lower alkylidene radical is a radical which corresponds to the abovementioned lower alkyl radicals or lower alkenyl radicals and which is divalent on one carbon atom, such as an ethylidene or isopropylidene radical, above all a methylene radical, or also a vinylidene radical.

The lower aliphatic hydrocarbon radical already discussed, and optionally also the lower alkylidene radical, can be substituted by one or more identical or different substituents, which are located, above all, in the α- and/or β-positions (corresponding to the 20-position and the 21-position respectively of the steroid numbering). Possible substituents are halogen atoms, for example chlorine and fluorine, optionally etherified and especially esterified hydroxyl groups, optionally ketalised oxo groups and optionally esterified carboxyl groups, it being possible for the carboxyl groups also to be present in the form of their salts, especially the alkali metal salts. An esterified carboxyl group is to be understood, above all, as meaning a carboxyl group which is in the form of its ester, especially in the form of its ester with lower alkanols, but also as meaning a carboxyl group which closes a 6-membered or especially a 5-membered lactone ring with a suitably remote hydroxyl group, which is present as a substituent in the same molecule.

A ketalised oxo group is derived, in particular, from lower alkanols, for example from methanol or ethanol, or preferably from α- or β-lower alkanediols, for example 1,2-or 1,3-propanediol or, above all, ethylene glycol; however, it can also be derived from the corresponding sulphur analogues of the alcohols mentioned and possess sulphur atoms in place of one or both of the oxygen atoms.

An etherified hydroxyl group is derived, in particular, from a lower alkanol, preferably a straight-chain lower alkanol, for example methanol, ethanol, propanol and butanol, from an aryl-lower alkanol, preferably a phenyl-lower alkanol, for example benzyl alcohol or triphenylmethylcarbinol, or from an oxygen-containing heterocyclic alcohol, for example 2-tetrahydropyranol or 2-tetrahydrofuranol. It can also formally be derived from a 1-lower alkoxy-lower alkanol, for example 1-butoxyethanol; the 1-butoxyethoxy group may be mentioned as an example of an etherified hydroxyl group of this type. Accordingly, an etherified hydroxyl group such as is present in an acetalised or ketalised vicinal steroid diol, for example 16α,17α-diol, is also to be regarded as an etherified hydroxyl group. The non-steroidal structural component, which in this case links two such vicinal etherified hydroxyl groups, is preferably a lower aliphatic, cycloaliphatic or arylaliphatic ketone, for example acetone, cyclopentanone, cyclohexanone, acetophenone or benzophenone, or an aldehyde, for example formaldehyde. As a special case of etherified hydroxyl groups, mention may also be made of the 17α,20; 20, 21-bis-methylenedioxy grouping.

An esterified hydroxyl group is derived, in particular, from an inorganic oxygen-containing acid, for example one of the sulphuric acids or phosphoric acids, or preferably from an organic acid, for example a sulphonic acid, for example an aromatic sulphonic acid, such as benzenesulphonic acid, toluenesulphonic acid or p-bromobenzenesulphonic acid, or an alkanesulphonic acid, such as methanesulphonic acid, or, in particular, from a carboxylic acid. A lactonised hydroxyl group is also to be regarded as an esterified hydroxyl group.

Possible carboxylic acid components of an esterified hydroxyl group are, primarily, the carboxylic acids customary in steroid chemistry, for example monocarboxylic acids with at most 18 carbon atoms, such as aliphatic carboxylic acids, especially formic acid, or a lower alkanecarboxylic acid, the lower alkyl radical of which is one of those mentioned above, primarily propionic acid, butyric acid, isobutyric acid, valeric acid, isovaleric acid, oenanthic acid and diethylacetic acid and, above all, caproic acid, trimethylacetic acid and acetic acid; but also corresponding halogenated lower alkanecarboxylic acids, such as chloroacetic acid, trichloroacetic acid or trifluoroacetic acid; as well as caprylic acid, pelargonic acid, capric acid, lauric acid, myristic acid, palmitic acid and stearic acid, the undecylic and undecylenic acids, elaidic acid and oleic acid; cycloaliphatic or cycloaliphatic-aliphatic monocarboxylic acids, for example cyclopropanecarboxylic acid, cyclobutanecarboxylic acid, cyclopentanecarboxylic acid and cyclohexanecarboxylic acid and cyclopropylmethanecarboxylic acid or cyclobutylmethanecarboxylic acid and a cyclopentylethanecarboxylic acid or cyclohexylethanecarboxylic acid; aromatic carboxylic acids, for example benzoic acids which are optionally substituted by fluorine, chlorine, bromine, hydroxyl, lower alkoxy, lower alkyl or nitro groups; aryl-lower alkanecarboxylic acids or aryloxy-lower alkanecarboxylic acids and the analogues thereof which are unsaturated in the chain, for example phenylacetic acids or phenoxyacetic acids, phenylpropionic acids and cinnamic acids which are optionally substituted, for example as indicated above for benzoic acid; and heterocyclic acids, for example furane-2-carboxylic acid, 5-tert.-butylfurane-2-carboxylic acid, 5-bromofurane-2-carboxylic acid, thiophene-2-carboxylic acid, nicotinic acid or isonicotinic acid, 3-(4-pyridyl)-propionic acid and pyrrole-2-carboxylic acids or pyrrole-3-carboxylic aids which are optionally substituted by lower alkyl radicals, or also corresponding dicarboxylic acids with at most 12 carbon atoms, for example succinic acid, glutaric acid, adipic acid and phthalic acid, as well as corresponding α-amino acids, especially α-amino-lower alkanecarboxylic acids, preferably those having the naturally occurring configuration, for example glycine, proline, leucine, valine, tyrosine, histidine, asparagine and also glutamic acid and aspartic acid.

The new 18,18-difluorosteroids according to the invention can be used as intermediates for the synthesis of valuable pharmaceutical active substances, especially for hormone therapy and for fertility control, and also as additives in animal feeds. A number of the steroids, for example the compounds singled out for special mention hereinafter, at the same time themselves exhibit a biological activity and, accordingly, can be used direct as active substances in the abovementioned fields of application.

The 18,18-difluorosteroids according to the invention are obtained according to a novel chemical process, which is characterised in that a corresponding 18-oxo compound of the general formula

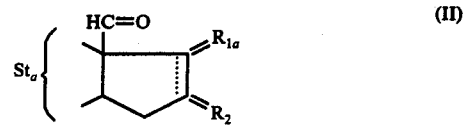

wherein $R_2$ has the abovementioned meaning, $St_a$ denotes a radical, corresponding to the radical St characterised above, in which no oxo groups other than the 11-oxo group and a 3-oxo group which is conjugated with at least one double bond are present and in which, if the reaction is carried out with sulphur tetrafluoride, no aromatic double bonds are present either, and $R_{1a}$ denotes a radical corresponding to the radical $R_1$ characterised above, in which no oxo groups are present and all the hydroxyl groups and carboxyl groups which may be present are in the esterified form, or denotes a dihydroxyacetone side chain, which is protected as the 17α,20;20,21-bis-methylenedioxy grouping, it being possible for a 16,17-double bond to be present in place of one of the said hydrogen atoms from each of the radicals $R_{1a}$ and $R_2$, is reacted with a compound of the formula $F_3SX$, wherein X denotes a fluorine atom or an amino group derived from a secondary amine, and, if desired, within the scope of the end products of the formula I, the resulting products are converted into one another in a manner which is in itself known by, for example, liberating protected functional groups, such as, above all, esterified carboxyl groups and esterified hydroxyl groups, or by liberating the dihydroxyacetone side chain from the 17α,20;20,21-bis-methylenedioxy grouping, but also by carrying out further conversions customary in steroid chemistry, in particular by esterifying or etherifying hydroxyl groups or by oxidising hydroxyl groups to give oxo groups, by ketalising oxo groups, or by converting oxo groups into enol ethers or enol esters, or by reducing oxo groups to give hydroxyl groups, optionally with simultaneous introduction of a hydrocarbon radical, and/or by saturating multiple bonds and/or by introducing further double bonds, optionally with aromatisation, and/or by halogenating or dehalogenating the resulting compounds. These subsequent conversions can be carried out individually or in appropriate combinations.

In the starting materials of the formula II, carboxyl groups which may be present are, as already indicated, in a form protected by esterification. The starting materials of the formula II must not contain any free or ketalised oxo groups or any oxo groups protected as enol ethers; exceptions are the 18-oxo group to be converted, which accordingly must remain free, the 11-oxo group, which is unreactive, and a 3-oxo group, that is conjugated with one or more double bonds, especially the 3-oxo group present in the Δ$^4$-3-oxo grouping or the Δ$^{1,4}$-3-oxo grouping. The reactivity of the conjugated oxo groups is reduced by the conjugation to such an extent that even without protection these groups remain unaffected under the reaction conditions employed. The starting materials of the formula II also must not contain any aromatic rings if sulphur tetrafluoride is used as the reagent. The other general and preferred structural characteristics and substituents are the same as those for the final products of the formula I. However, hydroxyl groups which may be present are preferably in an esterified form. Readily hydrolysable etherified hydroxyl groups, for example tetrahydropyranyloxy groups, are split hydrolytically in the course of the fluorination reaction to give free hydroxyl groups.

If a final product is to contain an oxo group other than those mentioned as exceptions, it is then appropriate to start from a starting material of the formula II, which contains a cyanohydrin or enol acylate grouping in the desired position or, in the case of the dihydroxyacetone side chain, the 17α,20;20,21-bis-methylenedioxy grouping. (The term "dihydroxyacetone side chain" signifies the 17α,21-dihydroxy-20-oxo-pregnane grouping). The groupings mentioned can subsequently be converted in a known manner, for example by hydrolysis, into the desired oxo group.

The reagent (fluorinating agent) of the formula $F_3SX$ is sulphur tetrafluoride or a disubstituted aminosulphur trifluoride, that is to say an aminosulphur trifluoride wherein the nitrogen atom is bonded to the sulphur atom and two carbon atoms. Accordingly, the substituents of the amino group are two identical or different open-chain or carbocyclic, optionally aromatic, hydrocarbon radicals, especially lower alkyl radicals, for example those mentioned above, or phenyl radicals, it being possible for the two radicals to be bonded together by a single C—C bond, by an oxygen bridge or by a lower alkylated nitrogen atom. The amino group designated by X is preferably a di-lower alkylamino group or a lower alkyl-phenyl-amino group, such as the dimethylamino, methylethylamino, methylpropylamino, methylphenylamino, ethylpropylamino, ethylphenylamino, dipropylamino, diisopropylamino or dibutylamino group, or an optionally C-lower alkylated pyrrolidino, piperidono, morpholino or N′-lower alkylpiperazino group, such as the N′-methylpiperazino group, symmetrical amino groups being particularly preferred. Above all, this amino group is the diethylamino group and the corresponding fluorinating agent is diethylaminosulphur trifluoride.

The reaction according to the invention is optionally carried out in the presence of inert solvents or mixtures thereof and/or in the presence of catalysts and also, with regard to the specific physical properties of the fluorinating agent used, optionally under elevated pressure. The reaction temperature depends on the specific properties of each reaction mixture; in general it varies between 0° and 150°, preferably between 30° and 100°.

The inert solvents used are those which, under the reaction conditions employed, react neither with the reactants nor with the products. In particular, the following solvents can be used: carbocyclic hydrocarbons, for example saturated carbocyclic hydrocarbons, such as cyclopentane, cyclohexane, cycloheptane and decahydronaphthalene, or aromatic carbocyclic hydrocarbons, such as benzene, toluene or xylene, which can also be halogenated on the nucleus, such as chlorobenzene, dichlorobenzene, bromobenzene or fluorobenzene, and especially aliphatic saturated hydrocarbons, preferably those which are liquid at atmospheric pressure and room temperature, such as pentanes, hexanes, heptanes or octanes, or those which are halogenated, especially chlorinated, such as chloroform, 1,1- or 1,2-dichloroethane, 1,1-, 1,2- or 1,3-dichloropropane and, above all, dichloromethane. Optionally, an excess of the fluorinating agent can be used as the solvent and/or several of the solvents mentioned can be combined with one another.

As catalysts, the use of which is particularly advantageous for the reaction with sulphur tetrafluoride, there are used Lewis acids, such as boron trifluoride, arsenic trifluoride, titanium tetrafluoride, phosphorus pentafluoride but, above all, hydrogen fluoride, Preferably, at least one molar equivalent of the catalyst is used, referred to the steroid employed. An advantageous mode of the use of hydrogen fluoride is to add a corresponding amount of water in place of this to the reaction mixture and to form the hydrogen fluoride direct in situ by partial hydrolysis of the excess sulphur tetrafluoride according to the equation

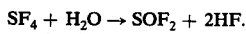

$$SF_4 + H_2O \rightarrow SOF_2 + 2HF.$$

The particular advantage of this variant is that by this means the difficulties in measuring out precise amounts of hydrogen fluoride are dispensed with. In place of water, it is also possible to use alcohols, especially lower alkanols, for the same purpose.

Since sulphur tetrafluoride is gaseous under normal conditions, it is appropriate, when using this substance, to heat the reaction mixture under pressure in pressure vessels, in particular those made of stainless steel or steel alloys, excess gaseous sulphur tetrafluoride being passed into the reaction mixture at low temperature and liquefied, and the pressure vessel being securely closed and heated to the desired reaction temperature. It is particularly advantageous to carry out the reaction in such a way that the reaction mixture does not come directly into contact with the material of the pressure vessel: the use of vessel inserts made of an inert plastic, such as polyethylene, polypropylene or Teflon ® (perfluoropolyethylene), is appropriate. When using aminosulphur trifluorides, which usually are liquid under normal conditions, it can be appropriate to work without pressure in glass apparatus, it being possible to achieve satisfactory results even with equimolar amounts of the starting steroid and the fluorinating agent, in some cases even without catalyst and/or solvent.

The replacement of an oxo group by two geminal fluorine atoms by means of sulphur tetrafluoride is already known as a general reaction, compare, for example, the review article by W. C. Smith: Angew. Chemie 74, 742–751 (1962), and has also been applied in steroid chemistry, compare, for example, D. G. Martin and F. Kagan: J. Org. Chem 27, 3164 (1962), and also D. G. Martin and J. E. Pike: J. Org. Chem. 27, 4086 (1962). In this work it has been found that the steric requirement of the fluorinating agent is considerable, as can already be demonstrated by the greatly reduced reactivity of, for example, benzophenone and the result of this is that in the steroids, the 11-keto group was found to be virtually unreactive because of its restricted steric accessibility (Martin, Kagan: loc. cit.). As is known, the steric conditions at the 18-oxo group are similar to those at the 11-oxo group and one would expect the reactivity to be just as low. Due to the angular nature of the bond at C-13, the carbonyl group to be reacted is shielded by the whole of the remaining part of the steroid molecule; an additional hindrance results from the angular methyl group at C-10 and especially from the substituents at the adjacent C-17. Taking into account the markedly acidic character of the fluorinating agent which itself is a strong Lewis acid, it is justifiable to assume that if the desired exchange proceeds at all it will then proceed so sluggishly that the formation of the tar-like by-products, a considerable amount of which is always formed in this reaction, completely predominates. The successful reaction according to the present invention is therefore entirely surprising and unexpected on the basis of the theoretical considerations.

The subsequent liberation of the protected oxygen-containing functional groups in the resulting process products is carried out in a manner which is in itself known, preferably by hydrolysis. Etherified hydroxyl groups are preferably hydrolysed under the conditions of acid catalysis in the presence of an inorganic acid, for example sulphuric acid, or a hydrogen halide acid, such as hydrochloric acid, hydrobromic acid or hydriodic acid, or of an organic acid, for example a sulphonic acid, such as p-toluenesulphonic acid or sulphosalicylic acid, or of a strong carboxylic acid, such as oxalic acid or formic acid. Enol ethers and ketals or acetals are also hydrolysed analogously to give the corresponding oxo derivatives. Carbonyl-containing ester groups of various types, whether these are esterified hydroxyl groups, esterified carboxyl groups, enol-acylated oxo groups or lactone groups, can be hydrolysed under acid conditions; however, they are preferably hydrolysed unter the conditions of base catalysis. Hydroxides, carbonates or bicarbonates of alkali metals, especially of sodium or potassium, are preferably used as basic catalysts. Esterified hydroxyl groups can also be liberated reductively, for example by the action of an ester-reducing agent, such as a complex hydride or diborane.

The subsequent esterification or etherification of hydroxyl groups in the resulting compounds is also effected in a manner which is in itself known. For esterification, for example, the compound to be esterified is treated with an excess of the acid itself, such as with formic acid, or with a reactive derivative thereof, for example with a derivative of one of the abovementioned acids, especially with an anhydride or acid halide, advantageously in the presence of a tertiary base, such as pyridine, quinoline or N-ethylpiperidine. Hydroxyl groups which are difficult to esterify, such as, for example, a tertiary 17α-hydroxyl group, can advantageously be esterified with an acid anhydride, under the catalytic action of organic sulphonic acids, for example benzenesulphonic acid, p-toluenesulphonic acid, sulphosalicylic acid or camphorsulphonic acid. For etherification, for example, the compounds to be etherified are treated with reactive derivatives of alcohols, for example with esters of strong acids, such as halides, sulphates or sulphonic acid esters, it being possible to use, in particular, one of the abovementioned alcohols as the alcohol component. Preferably, the reaction is carried out in the presence of basic agents. In order to form tetrahydropyranyl ethers and analogous ethers, a corresponding unsaturated derivative, such as 2,3-dihydropyrane or a vinyl lower-alkyl ether, for example vinyl butyl ether, is preferably used as the reagent and the reaction is carried out under the conditions of acid catalysis, preferably in the presence of an organic sulphonic acid.

The esterification of carboxyl groups, which is to be carried out if necessary, is also effected in a manner which is in itself known. For example, the carboxylic acid to be esterified is treated with an excess of alcohol, especially one of those mentioned above, in the presence of an acid catalyst, for example a strong inorganic acid, or the free acid is first converted into a reactive derivative thereof, such as the chloride or anhydride, and this is reacted with the desired alcohol. Lower alkyl esters, above all methyl esters, can also be prepared advantageously by reacting the free carboxylic acid to be esterified with the corresponding diazo-lower alkane, above all diazomethane. The lactonisation of a carboxyl group usually takes place spontaneously when a carboxyl group present as a salt is liberated by acidification; the lactonisation can also be accelerated by acid catalysis and/or by using dehydrating agents, such as acetic anhydride, anhydrous copper sulphate or molecular sieves, or by azeotropic distillation.

The ketalisation, enol-acylation and the formation of enol ethers, which are to be carried out if necessary, especially in order to protect the oxo groups, are also effected in a manner which is in itself known, especially under the conditions of acid catalysis and optionally using dehydrating agents or azeotropic distillation. For ketalisation, for example, lower alkanols, such as methanol or ethanol, and especially α- and β-glycols, such as 1,2- or 1,3-propanediol and 1,2- or 2,3-butanediol, and, above all, ethylene glycol, or reactive derivatives of these alcohols, such as acetals or ketals, especially those in which the carbonyl component is readily volatile, such as, for example, 2,2-dimethyl-1,3-dioxolane, are used. Corresponding thioketals are obtained analogously, but starting from the sulphur analogues of the abovementioned alcohols, above all from 1,2-ethanedithiol or a reactive derivative thereof.

In an analogous manner, vicinal steroid diols are reacted with non-steroidal ketones or aldehydes, such as is the case, for example, for the formation of acetonides of 16α,17α-diols, or for the conversion of 17α,21-dihydroxy-20-oxo-pregnanes with formaldehyde to corresponding 17α,20;20,21-bis-methylenedioxy derivatives. In order to form the enol ethers, an ortho-ester of a lower alkanol, especially of methanol or ethanol, with a lower aliphatic carboxylic acid, especially formic acid, is preferably used as the reagent; particularly preferred reagents are methyl orthoformate and, above all, ethyl orthoformate. The enol-acylation is advantageously carried out by reaction with a reactive derivative of the desired carboxylic acid under acid catalysis: preferably an anhydride, such as acetic anhydride, is used as the reagent and an organic acid, such as benzenesulphonic acid, p-toluenesulphonic acid, sulphosalicylic acid or camphorsulphonic acid, is used as the catalyst. Ketenes, especially the unsubstituted ketene, can also be used as reactive carboxylic acid derivatives. In the case of an oxo group conjugated with a double bond, the formation of the ketal, enol ether or enol ester may also be accompanied by a shift of the double bonds, for example in the case of the 3-oxo-$\Delta^4$ grouping the 4,5-double bond migrates into the 5,6-position.

Free oxo groups, especially the 17-oxo group, can subsequently be converted in a known manner into a cyanohydrin grouping, for example by reacting an oxo compound with hydrocyanic acid or one of its metal salts, preferably potassium cyanide or sodium cyanide, in an acid medium.

In resulting process products, it is also possible to oxidise free hydroxyl groups, especially secondary hydroxyl groups, to oxo groups in a manner which is in itself known. Preferred oxidising agents are compounds of 6-valent chromium, such as chromium trioxide, chromic acid and the alkali metal salts thereof. Lower alkanecarboxylic acids, such as acetic acid or propionic acid, or pyridine or acetone, optionally diluted with a halogenated lower alkane, such as dichloromethane or chloroform, and/or in the presence of aqueous sulphuric acid, advantageously are used as the reaction medium. Another preferred alternative for oxidising the hydroxyl group is the Oppenauer oxidation, that is to say oxidation with a ketone, such as acetone or cyclohexanone, under the catalytic action of an aluminium lower alkoxide, such as aluminium isopropylate; the Oppenauer oxidation is advantageously employed in the case of hydroxyl groups in the 17-position and especially in the 3-position, this being particularly advantageous in the latter case because, with this reaction, a double bond which may be present in the 5,6-position migrates spontaneously into the 4,5-position. The Oppenauer oxidation is also successful in the case of esterified hydroxyl groups which are derived from acids which can be split off easily, for example formic acid, and this is important for selective conversion, for example in the case of $3\beta,17\alpha$-dihydroxy-20-oxopregnane derivatives, where the $17\alpha$-hydroxyl group must be protected by esterification.

In resulting process products it is also possible to reduce oxo groups, especially the 3-oxo group and above all the 17-oxo group, to hydroxyl groups. The reduction is carried out in a manner which is in itself known and advantageously diborane or complex hydrides, especially those of aluminium or boron with an alkali metal or alkaline earth metal, such as, for example, sodium aluminium hydride, calcium borohydride and lithium borohydride, but especially lithium aluminium hydride and above all sodium borohydride, or derivatives thereof in which one or more hydrogen atoms are replaced by lower alkoxy radicals, such as sodium methoxyborohydride and especially lithium tri-tert.-butoxy-aluminium hydride, are advantageously used for this purpose. The choice of the solvent and of the reduction conditions depends on the reducing agent used and is in accordance with the generally known principles. In the case of a selective reduction, for example that of the 17-oxo group, the other oxo groups are protected temporarily as ketals or enol esters or enol ethers; when a 3-oxo-$\Delta^4$ grouping is present, the procedure can also be such that this grouping is also reduced and then selectively dehydrogenated, for example with manganese dioxide, back to the 3-oxo-$\Delta^4$ grouping.

However, the reduction of the oxo groups, above all of the 17-oxo group, can also be carried out in a manner which is in itself known with simultaneous introduction of a hydrocarbon radical, especially a lower aliphatic hydrocarbon radical, for example one of those mentioned initially, by reacting a corresponding oxo compound with a corresponding organo-metallic compound. If the hydrocarbon radical to be introduced is a lower alkyl radical, a Grignard compound, for example a lower alkyl-magnesium halide, such as methylmagnesium bromide or methylmagnesium iodide, or lower alkyllithium, such as methyllithium, is preferred as the organometallic compound; if a 1-alkinyl radical, especially the ethinyl radical, is to be introduced, a corresponding alkali metal compound, for example sodium acetylide or potassium acetylide or, in particular, lithium acetylide, is advantageously used. In the latter case it is particularly advantageous to use lithium acetylide in the form of its complex with ethylenediamine. The ethinyl radical introduced can then be further converted for example, by exchanging the terminal hydrogen atom therein for a carboxyl group. This is effected by treatment with a Grignard compound and subsequent reaction of the resulting $\omega$-magnesium halide with carbon dioxide. In these reactions, the other oxo groups must be protected in a manner analogous to that described above for the selective reduction. If the oxo group to be converted is combined with one or two consecutive double bonds to form a conjugated system, such as is the case in the 3-oxo-1-ene, 3-oxo-4,6-diene or 20-oxo-16-ene grouping, the reaction with a Grignard compound, especially a methylmagnesium halide, can then be so conducted, in a known manner, especially in the presence of a copper-(I) salt, that the hydrocarbon radical to be introduced is introduced not on the carbon atom carrying the oxo group but on the carbon atom which is at the end of the conjugated system, which formally corresponds to a 1,4-or 1,6-addition. In this reaction the oxo group is converted to a hydroxyl group, which, however, is then a part of an enol grouping and is rearranged to form an oxo group during the working up, with simultaneous formal saturation of the double bond. The conjugated systems indicated above by way of example then result in, for example, the $1\beta$-methyl-3-oxo, the $7\alpha$-methyl-3-oxo-4-ene and the $16\alpha$-methyl-20-oxo grouping respectively.

According to a modification of the reaction with Grignard compounds, however, it is also possible, in the resulting process products, to introduce a substituted lower aliphatic hydrocarbon radical in a manner which is in itself known by reacting a nitrile, especially a 17-cyano compound, with a lower alkyl-magnesium halide, by which means a corresponding $\alpha$-oxo-alkyl radical is formed; for example, a corresponding 20-oxopregnane compound is obtained by reacting a $17\beta$-cyano compound with a methylmagnesium halide. In the case of a 17-cyanohydrin, in which, in addition to the cyano group, also a hydroxyl group is linked to C-17, this hydroxyl group is first etherified, for example converted to a tetrahydropyranyl ether, or split off by means of a dehydrating agent, the 16,17-double bond being formed. This method is particularly suitable for the conversion of 17-oxoandrostane compounds into optionally $17\alpha$-hydroxylated or 16,17-unsaturated 20-oxopregnane compounds.

It is also possible to introduce double bonds into the resulting final products, in a manner which is in itself known. For example, $\Delta^4$-3-oxo compounds, optionally in the form of their 3-enol-acylates or 3-enol ethers, can be reacted with quinones, such as chloranil or especially 2,3-dichloro-5,6-dicyano-1,4-benzoquinone, by which means, depending on the choice of the reaction conditions, which are in themselves known, the 6,7-double bond and/or the 1,2-double bond is formed, or, in the case of a 19-nor compound, by rearrangement of the 3-oxo-1,4-diene grouping first formed, aromatisation of the A ring can take place in the same step, the 3-hydroxy-1,3,5(10)-triene grouping being formed. 1,2-Dehydrogenation of $\Delta^4$-3-ketones can also be achieved in a manner which is in itself known by treatment with selenium dioxide, or microbiologically, for example by means of the micro-organisms Corynebacterium simplex or Septomyxa affinis; 6,7-dehydrogenation is also achieved by reacting an enol ether of a $\Delta^4$-3-ketone with manganese dioxide. However, it is also possible to introduce double bonds in a known manner by dehalogenation. Thus, for example, a 5,6-dibromide is treated with an alkali metal iodide, such as potassium iodide, or zinc dust, by which means the 5,6-double bond is formed. However, the dehalogenation can also be carried out by splitting off halogen in the form of hydrogen halide; for example a $\Delta^{4,6}$-3ketone is obtained from a 6-halogeno-$\Delta^4$-3-ketone in this way. For this purpose, a reaction with lithium carbonate or calcium carbonate, optionally in the presence of a lithium halide, such as lithium chloride or lithium bromide, in dimethylformamide or hexamethylphosphoric acid triamide, is particularly suitable. Double bonds can also be introduced, in a known manner, if a hydroxyl group, especially a secondary or, above all, a tertiary hydroxyl group, is split off from resulting process products using a dehydrating agent. Particularly suitable dehydrating agents are reactive derivatives, especially halides, of medium strength inorganic acids, such as sulphurous acid or phosphoric acid, for example thionyl chloride, lower alkoxysulphinyl chloride or phosphorus oxychloride; an aromatic heterocyclic base, such as pyridine, is preferably used as the reaction medium.

In resulting process products it is also possible to saturate multiple bonds, that is to say double bonds and triple bonds, in a manner which is in itself known, for example by catalytic hydrogenation. A triple bond can give a double bond in a first stage and this is optionally further saturated to give a single bond. The catalytic hydrogenation is carried out with hydrogen gas at normal or elevated pressure under conditions of heterogeneous or homogeneous catalysis. Particularly suitable catalysts for heterogeneous catalysis are finely divided metals, for example Raney metals, such as Raney nickel, or noble metals, such as palladium, platinum or rhodium, which optionally are dispersed on a carrier, such as calcium carbonate or barium sulphate. Complex rhodium compounds, for example tris(triphenylphosphine)-rhodium-I chloride, are used in particular for homogeneous catalysis. A Lindlar catalyst, that is to say a palladium catalyst partially deactivated by lead, is advantageously used for the selective hydrogenation of a triple bond to a double bond.

It is also possible to introduce halogen atoms into resulting process products, in a manner which is in itself known. Thus, for example, elementary halogen, such as chlorine or bromine, or a hypohalous acid, such as hypobromous or especially hypochlorous acid, can be added onto a double bond or a system of two or more conjugated double bonds. For example, when introducing a halogen atom, such as a chlorine or bromine atom, into the 6-position, the procedure is advantageously such that elementary halogen, such as chlorine or bromine, or especially one of the abovementioned hypohalous acids, is allowed to act on a 3-enol ether or 3-enol ester, especially a 3-lower alkoxy-3,5-diene or a 3-lower alkanoyloxy-3,5-diene; the 3-oxo group is liberated during the reaction or, at the latest, during working up of the reaction mixture, so that a 6β-halogeno-Δ⁴-3-ketone results. In the same way it is also possible, starting from a 6-halogeno-Δ⁴-3-ketone, or its enol ether, to introduce a second halogen atom into the 6-position.

The addition of a hypohalous acid is effected very advantageously by treatment with a hypohalous acid formed in situ, such as hypohalous acid formed in the reaction mixture from one of its organic derivatives, especially from a corresponding N-halogenoamide or N-halogenoimide, for example bromoacetamide, chloroacetamide or bromosuccinimide. The reaction is advantageously carried out in organic solvents which are miscible with water, for example acetone, dioxane or tetrahydrofurane, in the presence of water and a lower aliphatic carboxylic acid, of example acetic acid, and optionally also in the presence of an alkali metal salt of this acid, for example in the presence of sodium acetate or potassium acetate. A particularly advantageous method, which is in itself known, for introducing a halogen atom, especially a chlorine atom or a fluorine atom, into the 6-position of the 3-oxo-4,6-diene grouping is selectively to epoxidise the 6,7-double bond, for example by means of an organic per-acid, such as monoperphthalic acid, perbenzoic acid, p-chloroperbenzoic acid or peracetic acid, to treat the resulting epoxide with the corresponding hydrogen halide and to dehydrate the resulting 6β-halogen-7α-hydroxy compound, the desired 6-halogeno-3-oxo-4,6-diene grouping being formed. In this particular case, the dehydration is advantageously carried out by reaction with a hydrogen halide acid, preferably with hydrogen chloride, in a lower alkanecarboxylic acid, for example acetic acid.

If the said reaction of the epoxide with the hydrogen halide is carried out in a medium of the said lower alkanecarboxylic acids, opening of the ring and dehydration take place in the same step. However, in general, the epoxide ring is opened using a hydrogen halide or hydrogen halide donor, for example pyridine hydrochloride or a complex of hydrogen fluoride with urea or a cyclic ether, such as tetrahydrofurane. In this way the corresponding trans-halogenohydrin is always formed from an epoxide, for example a 5α-hydroxy-6β-halogeno compound is formed from a 5α,6α-epoxy compound or, in particular, an 11β-hydroxy-9α-halogeno compound is formed from a 9β,11β-epoxy compound. This latter reaction is of exceptional importance, in particular for introducing a fluorine atom into the 9α-position.

Amongst the 18,18-difluorosteroids which are obtainable according to the process, compounds of particular interest are those of the general formula

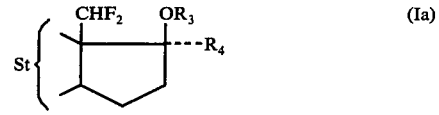 (Ia)

wherein St has the abovementioned meaning, $R_3$ denotes a hydrogen atom or a lower alkyl or lower alkanoyl group and $R_4$ denotes a hydrogen atom or a lower aliphatic hydrocarbon radical, especially a lower alkyl radical, above all the methyl radical and ethyl radical, or the ethinyl radical.

Compounds to be singled out, because of their advantageous biological properties, from the last mentioned compounds of the formula Ia are those in which St represents a radical of the partial formula $St_1$

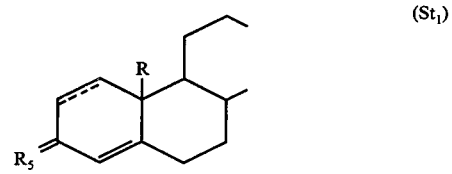 (St₁)

wherein $R_5$ denotes the oxo group or a hydrogen atom conjointly with an esterified hydroxyl group, or especially with a free hydroxyl group, or denotes two hydrogen atoms, and R denotes a hydrogen atom or the methyl group, it being possible for an additional 1,2-double bond also to be present in compounds in which R is the methyl group. These compounds are distinguished as highly active sex hormones. On the one hand, they have a central action in that they block the secretion of pituitary gonadotrophins; on the other hand, they also have a peripheral action on the male and the female sexual functions, as can be demonstrated by animal experiments. Because of these advantageous biological properties, the compounds can be used in medicine for all indications involving sex hormones, but especially as preparations for inhibiting gonadotrophin secretion and/or for controlling fertility. Compounds to be singled out particularly are 17β-acetoxy-18,18-difluoro-oestr-4-en-3-one, which in a dose of 0.01 mg/animal (capon, comb test, local application) exhibits a marked androgenic activity and in a dosage range of from 0.01 to 0.1 mg/kg (rat, ovulation test, subcutaneous administration) inhibits ovulation, and 17α-ethinyl-18,18-difluoro-17β-hydroxy-oestr-4-en-3-one, which in a dosage range of from 0.03 to 0.3 mg/kg (rabbit, Clauberg test, perorally) exhibits a distinct gestagenic activity and in a dosage range of from 0.3 to 1 mg/kg (rat, ovulation test, perorally) inhibits ovulation.

Compounds which should also be mentioned because of their advantageous biological properties are those amongst the compounds, characterised above, of the formula Ia in which St represents a radical of the partial formula $St_2$

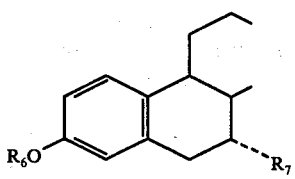

(St$_2$)

wherein $R_6$ denotes a hydrogen atom or a lower alkyl group, especially the methyl group, and $R_7$ denotes a hydrogen atom or the methyl group. These compounds are also distinguished as highly active sex hormones. They have a central action and greatly inhibit the secretion of pituitary gonadotrophins. In addition, they also have a peripheral action on the male and the female gonadal activity, as can be shown by animal experiments. Because of these advantageous biological properties, they can be used as therapeutic preparations in medicine for all the indications usual for oestrogens, but especially to inhibit gonadotrophin secretion and/or to control fertility.

The compounds of the general formula Ia, in which St corresponds to the radical $St_a$, which was characterised initially, can be obtained direct by means of the fluorination process described initially. For example, the compounds of the formula Ia, wherein St has the meanings of $St_1$, can be obtained in this way; however, under certain circumstances it is more advantageous to introduce the 1,2-double bond only subsequently into a corresponding 1,2-saturated 18,18-difluoro compound, for example as has been indicated above.

Those compounds of the formula Ia in which St has the meaning of $St_2$ are also accessible directly by the general fluorination process, with the restriction, however, that the reaction is not carried out with sulphur tetrafluoride. However, they can also be prepared advantageously in a manner which is in itself known, for example as described above, by aromatisation of the corresponding compounds of the formula Ia, in which St represents a radical of the partial formula $St'_2$

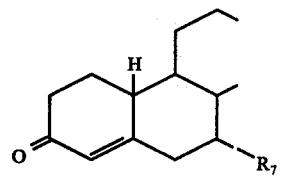

(St'$_2$)

wherein $R_7$ has the abovementioned meaning, and, if desired, etherification at the 3-hydroxyl group by a lower alkyl radical.

Alternatively, the compounds of the formula Ia wherein St has the meaning of $St_1$ can be obtained when the corresponding intermediates of the formula Ia, wherein St represents a radical of the partial formula $St_3$

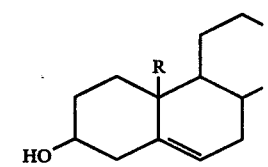

(St$_3$)

wherein R has the abovementioned meaning, are used as the starting materials. Appropriately, in these intermediates, the 3-hydroxyl group is oxidised in a known manner, for example as described above, especially by the Oppenauer oxidation, to the 3-oxo group, the double bond simultaneously shifting into the 4,5-position, and, if desired, in resulting compounds, the 3-oxo group is reduced, in the manner described above, to a 3-hydroxyl group and this is optionally esterified or, if R represents the methyl group, the 1,2-double bond is introduced in the manner already described.

Another method of manufacturing the compounds of the formula Ia characterised above, wherein St represents $St_1$, $St_2$, $St'_2$ or $St_3$, consists in reducing the 17-oxo group, in a corresponding 17-ketone of the general formula III

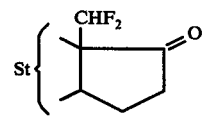

(III)

wherein St has the meanings indicated for $St_1$, $St_2$, $St'_2$ and $St_3$, to a hydroxyl group in the manner described above, the 3-oxo group temporarily being selectively protected if desired, and a lower aliphatic hydrocarbon radical being introduced, if desired, in the 17α-position, and, if desired, esterifying or etherifying the hydroxyl groups which are present, in the manner described above. Compounds of the general formula III, wherein St has the meaning of $St_1$, $St'_2$ and especially $St_2$, themselves have a hormonal action similar to that indicated in detail for the corresponding compounds of the general formula Ia.

18,18-Difluorosteroids of the general formula Ib

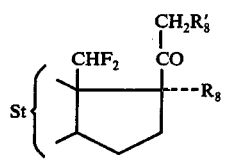

wherein $R_8$ and $R'_8$ independently of one another each denote a hydrogen atom or a free or esterified hydroxyl group, especially a hydroxyl group esterified by one of the lower alkanecarboxylic acids mentioned initially, and St has the meaning indicated initially, are also preferred.

On account of their advantageous biological properties, especially their hormone-like action, particularly preferred compounds of the formula Ib above are those wherein St represents the radical of the general formuls $St_4$

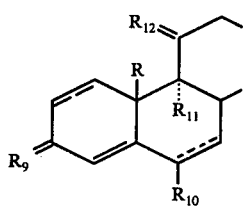

wherein R has the abovementioned meaning, $R_9$ represents an oxo group or represents a hydrogen atom conjointly with a hydroxyl group which is preferably β-oriented and optionally esterified, $R_{10}$ represents a hydrogen atom, the methyl group or a halogen atom, such as a fluorine, chlorine or bromine atom, α-orientation of this substituent being preferred, $R_{11}$ denotes a hydrogen atom or a halogen atom, especially the fluorine or chlorine atom, and $R_{12}$ denotes two hydrogen atoms or an oxo group or denotes an α-oriented hydrogen atom conjointly with a chlorine atom or a hydroxyl group, it being possible for one double bond to be present in the 6,7-position and, if R represents the methyl group, also in the 1,2-position and/or 6,7-position.

Especially preferred compounds amongst the last mentioned compounds are those of the general formula Ib, wherein $R'_8$ is a free or esterified hydroxyl group, $R_8$ has the abovementioned meaning and St represents the radical of the partial formula $St'_4$

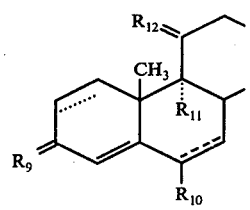

wherein $R_{10}$ and $R_{11}$ have the abovementioned meanings and $R'_{12}$ represents an oxo group or represents an α-oriented hydrogen atom conjointly with a hydroxyl group or a chlorine atom, it being possible for a double bond to be present in the 6,7- position and/or especially in the 1,2-position. As a typical representative of this group of compounds, particular mention may be made of 18,18-difluoro-17α-21-dihydroxypregna-1,4-diene-3,11,20-trione (18,18-difluoro-prednisolone) and the 17α-esters and/or 21-esters thereof, especially those with lower alkanecarboxylic acids. These compounds are distinguished by their hormonal activity, which is analogous to the general characteristics of the natural hormones of the adrenal cortex; mineralo -corticoid properties, that is to say the influence on the equilibrium of sodium, potassium and water in body tissues, and, above all, the high antiinflammatory activity are therapeutically especially valuable.

Another, equally important group is formed by the compounds of the general formula Ib, in which $R'_8$ represents a hydrogen atom, $R_8$ has the abovementioned meaning and preferably denotes a hydroxyl group esterified by a lower alkanecarboxylic acid and St represents the radical $St_1$, characterised above, or the radical of the partial formula $St''_4$

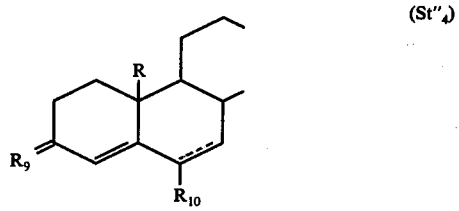

wherein R, $R_9$ and $R_{10}$ have the abovementioned meaning. Particularly preferred compounds of this type are those in which $R_9$ represents an oxo group and $R_{10}$ represents the methyl group or a chlorine atom.

The latter compounds are distinguished by their hormonal activity and substantial inhibition of the secretion of pituitary gonadotrophins. Due to these outstanding biological properties, they can be used as active substances in pharmaceutical preparations for indications where gestagens are usual, such as substitutive hormone therapy and inhibition of ovulation, as well as for fertility control.

The compounds of the formula Ib, characterised above, are not directly accessible by the general fluorination process. However, those compounds of the formula Ib wherein $R'_8$ represents hydrogen can be prepared, for example, in a manner which is in itself known, if a compound of the general formula IV

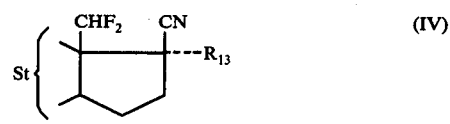

wherein St has the meaning mentioned initially and $R_{13}$ represents an etherified hydroxyl group which can be hydrolysed easily or, omitting a hydrogen atom in the 16-position, represents the 16,17-double bond, is reacted with a methylmagnesium halide and subsequently the 16,17-double bond is saturated or the etherified hydroxyl group is hydrolysed to a free hydroxyl group and this is esterified if desired. The said etherified hydroxyl group which can be hydrolysed easily is an etherified hydroxyl group of the partial formula

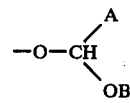

wherein A and B each individually denote a lower alkyl radical or conjointly denote the trimethylene radical or the tetramethylene radical, for example a 1-lower alkoxy-lower alkoxy group, especially the 1-butoxyethoxy group, or the tetrahydrofuranyloxy group or the tetrahydropyranyloxy group. These reactions are carried out in a manner which is in itself known, for example as indicated initially, a 3-oxo group which may be present being temporarily protected in the form of a ketal or especially of an enol ether during the Grignard reaction. Methyl-magnesium bromide is used as the preferred reagent and benzene is used as the preferred solvent. The starting materials of the general formula IV are also prepared in a manner which is in itself known by the addition of hydrogen cyanide to the 17-oxo group in compounds of the general formula III and either splitting off the 17-hydroxyl group, a 16,17-double bond being formed, or etherifying the 17-hydroxyl group in a manner which is in itself known to give the group $R_{13}$ having the abovementioned meaning.

Those compounds of the formula Ib in which St denotes the radical $St_1$, characterised above, can also be obtained from corresponding compounds of the formula Ib wherein St denotes the radical $St_3$, characterised above. The conversion of the radical $St_3$ into the radical $St_1$ is effected in the same way as has already been indicated above for the compounds of the formula Ia.

Those compounds of the formula Ib wherein St denotes the radical $St'_4$, characterised above, in which $R_{11}$ is a halogen atom and $R'_{12}$ is a hydrogen atom conjointly with a hydroxyl group, are obtained in a manner which is in itself known by reacting a compound of the partial formula $St_5$

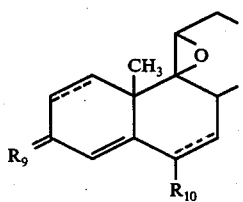

(St$_5$)

wherein $R_9$ and $R_{10}$ have the abovementioned meanings, with an appropriate hydrogen halide acid. Particularly advantageous are fluorine compounds, which are prepared by means of hydrofluoric acid, preferably in the presence of an ether-like solvent, such as tetrahydrofurane, or of urea.

If it is desired to obtain compounds of the formula Ib, wherein St denotes the radical $St'_4$, characterised above, in which $R_{11}$ is a chlorine atom and $R'_{12}$ is a hydrogen atom conjointly with a chlorine atom, a corresponding compound of the partial formula $St_6$

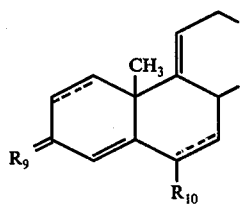

(St$_6$)

wherein $R_9$ and $R_{10}$ have the abovementioned meanings, can advantageously be reacted with chlorine. Preferably, chlorine is formed directly in the reaction mixture by the action of hydrogen chloride on an N-chloroamide or N-chloroimide, such as N-chlorosuccinimide or N-chloroacetamide.

Those compounds of the formula Ib in which there are additional double bonds in the 1,2-position and/or 6,7-position in the radical $St_4$ are advantageously obtained by means of the 1,2-dehydrogenation or 6,7-dehydrogenation, described above, of the corresponding saturated 3-oxo-$\Delta^4$-analogues (in which the substituent $R_{10}$ in the 6-position may be in the $\alpha$-position or the $\beta$-position), optionally with subsequent reduction of the 3-oxo group to the 3-hydroxyl group and esterification thereof. Those compounds of the formula Ib in which St represents the radical of the partial formula $St'''_4$

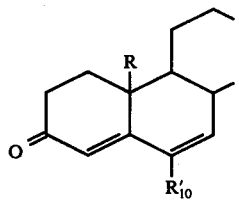

(St$_4''$)

wherein R has the abovementioned meaning and $R'_{10}$ represents a halogen, are also obtained when the desired halogen atom is introduced into a corresponding compound which is not halogenated in the 6-position, in the manner described above via a 6$\alpha$,7$\alpha$-epoxide.

The compounds of the general formula Ib, wherein $R'_8$ represents hydrogen, are also obtained by oxidising the 20-hydroxyl group in a compound of the general formula V

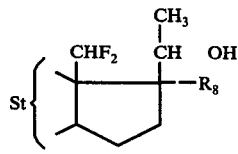

wherein St and $R_8$ have the abovementioned meaning, to the keto group in a manner which is in itself known. For this purpose, the agents and methods described above can be used. If $R_8$ denotes a free hydroxyl group certain precautions need to be taken and the reaction conditions are to be so chosen that the desired end product is not further oxidised with removal of the side chain. The compounds of the general formula V can be obtained by saponification of the corresponding 20-esters; these esters, in turn, can be obtained by the general fluorination procedure and they therefore hold an important key position as intermediate products.

The compounds of the general formula Ib, wherein $R'_8$ represents an optionally esterified hydroxyl group, are advantageously obtained starting from the corresponding compounds of the formula Ib wherein $R'_8$ represents hydrogen by halogenating these compounds in the 21-position in a manner which is in itself known and exchanging the halogen atom, especially bromine or iodine, for an esterified hydroxyl group and optionally liberating it. The halogenation in the 21-position is carried out, for example, by the action of bromine in the presence of a hydrogen halide acid, for example hydrochloric acid or, above all, hydrobromic acid, or by the action of elementary iodine in the presence of calcium oxide and optionally also calcium chloride. The subsequent replacement of the halogen atom which has been introduced by an esterified hydroxyl group, especially a lower alkanoyloxy group, is preferably effected by treatment with a salt of a corresponding acid, especially by means of an alkali metal salt or of a salt with an organic base, for example with a tertiary amine, such as a tri-lower alkylamine. Potassium lower alkanoates and tri-lower alkyl amine lower alkanoates, for example acetates, may be mentioned as being particularly advantageous for this reaction.

The compounds of the general formulae Ib and III are also obtained when corresponding compounds in which one or more oxo groups are present in the form of a ketal, an enol ether or an enol acylate, are hydrolysed in a manner which is in itself known, especially as described above. Those compounds of the formula Ia and V in which St has the meaning of $St_1$, $St'_2$, $St_4$, $St'_4$, $St''_4$, $St'''_4$, $St_5$ and $St_6$ can also be obtained in the same way.

The compounds of the formula Ib wherein $R_8$ and $R'_8$ each represent a free hydroxyl group are obtained advantageously when a corresponding $17\alpha,20;19,21$-bis-methylenedioxypregnane compound is saponified. Preferred conditions for this reaction are those of acid catalysed hydrolysis, for example by means of a dilute lower aliphatic carboxylic acid, such as formic acid or acetic acid, or by means of hydrofluoric acid, optionally in the presence of urea.

Depending on the choice of the procedure and of the starting materials, the new compounds according to the invention can be in the form of mixtures of isomers or as racemates. This occurs in particular in the case of compounds which have been prepared by total synthesis. If mixtures of isomers are obtained, they can be separated, on the basis of the physicochemical differences between the components, into their individual components in a known manner, for example by chromatography and/or fractional crystallisation. If racemates are obtained, they are first combined in a manner which is in itself known with an optically active compound, for example esterified with an optically active acid, and the mixture of isomers thus obtained is separated as indicated above. The individual antipodes are liberated from the separate components thus obtained in a manner which is in itself known, for example by hydrolysis.

The invention also relates to those embodiments of the above processes in which a compound obtained as an intermediate at any stage is used as the starting material and the missing steps are carried out or in which a starting material is formed under the reaction conditions.

The starting materials for the processes of the present invention are known or can be manufactured in a manner which is in itself known. Appropriately, those starting materials which contain the substituents mentioned particularly above, and especially those starting materials which lead to the final products described specifically or highlighted by formulae herein, are used.

The present invention also relates to the production of pharmaceutical preparations, and of contraceptives for humans and mammals, which contain the new pharmacologically active substances, described above, of the present invention as active substances, together with a pharmaceutical excipient. Organic or inorganic substances which are suitable for enteral, for example oral, or parenteral administration or for topical application are used as the excipients. Substances which can be used to form the excipients are those which do not react with the new compounds, such as, for example, water, gelatine, lactose, starch, magnesium stearate, talc, vegetable oils, benzyl alcohols, gum, polyalkylene glycols, white petroleum jelly, cholesterol and other known medicinal excipients. The pharmaceutical preparations can be in the solid form, for example as tablets, dragees or capsules, or in the liquid or semi-liquid form as solutions, suspensions, emulsions, ointments or creams. Optionally, these pharmaceutical preparations are sterilised and/or contain auxiliaries, such as preservatives, stabilisers, wetting agents or emulsifiers, salts to regulate the osmotic pressure or buffers. They can also contain other therapeutically valuable or biologically active substances.

The following Examples describe the invention in more detail, but do not limit it to what is described therein. The temperatures are given in degrees Centigrade.

EXAMPLE 1

2.3 g of $3\beta,17\beta$-dihydroxy-androst-5-en-18-al diacetate are dissolved in 24 ml of methylene chloride. After adding 0.4 ml of water, the solution is cooled in a plastic vessel to $-76°$ C and treated with 48 ml of liquid sulphur tetrafluoride (the gaseous reagent is passed in and condensed) and the mixture is then stirred in an autoclave for 20 hours at 20° C.

The excess fluorinating agent is then evaporated off, the reaction solution is poured into ice-cold sodium bicarbonate solution and the mixture is diluted with ethyl acetate, washed twice with saturated sodium chloride solution, dried and, together with the ethyl acetate used for subsequent extraction of the washings, evaporated in an aspirator vacuum. The resulting amorphous crude product is dissolved in toluene and filtered through 10 times the amount by weight of grade III aluminium oxide (neutral) and the concentrated filtrate is chromatographed over 100 times the amount by weight of silica gel using a toluene/ethyl acetate (95:5) mixture as the eluant. In addition to a small amount of the starting material in the first fractions, 18,18-difluoro-androst-5-ene-$3\beta,17\beta$-diol diacetate is obtained as the main fraction. After one recrystallisation from acetone/hexane, the pure compound melts at 174°–176° C. $[\alpha]_D^{25} = -88°$ (CHCl$_3$). IR spectrum 1735, 1235 and 1050 cm$^{-1}$. NMR spectrum 1.05 ppm (C-19), 2.01 ppm (OCOCH$_3$), 2.04 ppm (OCOCH$_3$), 4.80 ppm, multiplet, (C-3, C-17), 5.35 ppm, multiplet, (C-6), 5.98 ppm, triplet, $J_{HF} = 52$ Hz.

If the same batch is run using smaller amounts of sulphur tetrafluoride (30 ml) and maintaining a shorter reaction time (7 hours), the starting material and pure 18,18-difluoro derivative, which is identical to that described above, are obtained in approximately equal amounts after chromatography and purification.

EXAMPLE 2

2.0 g of $3\beta,17\beta$-dihydroxy-androst-5-en-18-al diacetate, in a glass flask under a nitrogen atmosphere, are treated with 5 ml of diethylaminosulphur trifluoride at room temperature and the mixture is stirred for one hour at 60° C under nitrogen. The reaction mixture is cooled to 25° C, diluted cautiously with dichloromethane and poured into ice water. The organic layer is separated off and the aqueous layer is further extracted with dichloromethane. The organic extracts are combined, washed with water until neutral, dried over sodium sulphate and evaporated at aspirator pressure. The slightly coloured residue is chromatographed over silica gel using hexane/ethyl acetate (9:1) as the solvent. The product is identical to the 18,18-difluoro-androst-5-ene-3β,17β-diol diacetate obtained according to Example 1.

EXAMPLE 3

12 ml of sulphur tetrafluoride are condensed into a solution, cooled to −76° C, of 330 mg of 17β-hydroxy-3-oxo-oestr-4-en-18-al acetate in 6 ml of methylene chloride and 0.12 ml of water (plastic vessel). The reaction mixture is then stirred in an autoclave for 20 hours at room temperature (about 20° C). The excess reagent is then removed by releasing the pressure from the autoclave, the reaction mixture is poured into ice-cold sodium bicarbonate solution, the mixture is taken up in ethyl acetate, washed until neutral and extracted again and the organic phase is dried and evaporated at aspirator pressure. The residue is dissolved in a small amount of methylene chloride and chromatographed over 100 times the amount by weight of silica gel (system: hexane/ethyl acetate (4:1)). In addition to a small amount of starting material in the first runnings, 18,18-difluoro-17β-hydroxy-oestr-4-en-3-one acetate is obtained as the main product. After reprecipitation from ether/hexane, the compound melts at 108°–110° C. IR spectrum: bands at, inter alia: 1740, 1670, 1620, 1235 and 1060 cm$^{-1}$. NMR spectrum: 2.05 ppm, singlet, (OCOCH$_3$), 4.9 ppm, multiplet, (C-17), 5.85 ppm, broad singlet, (C-4), 6.06 ppm, triplet, $J_{HF}$ = 52 Hz, (C-18).

EXAMPLE 4

By starting from 17β-hydroxy-3-oxo-oestr-4-en-18-al acetate and proceeding in a manner analogous to that described in Example 2, 18,18-difluoro-17β-hydroxy-oestr-4-en-3-one acetate is obtained, which is identical to the product obtained according to Example 3.

EXAMPLE 5

After adding 22 ml of a 10% strength potassium hydroxide solution, a solution of 2.3 g of 18,18-difluoro-androst-5-ene-3β,17β-diol diacetate (crude product) in 130 ml of methanol is stirred for 1 hour at room temperature, whilst passing nitrogen through the solution. The reaction mixture is then concentrated to about 60 ml in an aspirator vacuum and taken up in ethyl acetate and the mixture is washed with 1 N hydrochloric acid and with water until neutral, dried and evaporated in an aspirator vacuum. The crude 18,18-difluoro-androst-5-ene-3β,17β-diol is suspended, without purification, in 80 ml of toluene, the suspension is treated with 8 ml of cyclohexanone and 2.2 g of aluminium isopropylate and the mixture is refluxed for 45 minutes with stirring. The cooled reaction mixture is worked up by diluting it with ethyl acetate and washing it successively with saturated Seignette salt solution (potassium sodium tartrate solution) and with water. The washings are further extracted with ethyl acetate and the organic phases are dried and evaporated in an aspirator vacuum. The amorphous residue is then chromatographed over 100 times the amount by weight of silica gel. Elution with a mixture of hexane/ethyl acetate (3:1) gives successively, in approximately equal amounts by weight, 18,18-difluoro-androst-4-ene-3,17-dione, which after recrystallisation from acetone/hexane melts at 161°–163° C, and 18,18-difluoro-17β-hydroxy-androst-4-en-3-one of melting point 183°–184° C (recrystallised from acetone/hexane).

EXAMPLE 6

A solution of 56 mg of potassium hydroxide in 2 ml of water is added to 290 mg of 18,18-difluoro-17β-hydroxy-oestr-4-en-3-one acetate in 50 ml of methanol and the mixture is stirred under nitrogen at room temperature for 4.5 hours. The reaction solution is then evaporated in vacuo to half its volume, diluted with ethyl acetate, washed until neutral, dried and evaporated in an aspirator vacuum. The resulting amorphous 18,18-difluoro-19-nor-testosterone is homogeneous as shown by thin layer chromatography and can be used without further purification for the next stage.

EXAMPLE 7

310 mg of crude 18,18-difluoro-17β-hydroxy-oestr-4-en-3-one (18,18-difluoro-19-nor-testosterone) are dissolved in 40 ml of acetone and oxidised for 5 minutes at 0° C with about 1.5 equivalents of a 8 N solution of chromium-VI oxide in dilute sulphuric acid (Jones reagent). Saturated potassium acetate solution is added to the reaction mixture and the resulting mixture is diluted with ethyl acetate and the organic layer is washed with a saturated sodium chloride solution until neutral, dried and evaporated in an aspirator vacuum. The resulting residue is dissolved in a mixture of hexane/ethyl acetate (2:1) and filtered through 20 times the amount by weight of silica gel. The evaporated fractions give 18,18-difluoro-oestr-4-ene-3,17-dione, which after recrystallisation from methylene chloride/hexane melts at 186°–189° C. IR spectrum: 1745, 1670 and 1620 cm$^{-1}$.

EXAMPLE 8

500 mg of 18,18-difluoro-androst-4-ene-3,17-dione are dissolved in 20 ml of dioxane and, after adding 1 ml of orthoformic acid ethyl ester and 30 mg of p-toluenesulphonic acid, the mixture is stirred for 8 hours at room temperature. The reaction mixture is then poured into water (containing traces of pyridine) and extracted twice with ethyl acetate and the extracts are washed until neutral, dried and evaporated in an aspirator vacuum. The crude amorphous enol ether (3-ethoxy-18,18-difluoro-androsta-3,5-dien-17-one) is dissolved direct in 30 ml of absolute ether and the solution is added dropwise to an ethereal solution of methyl magnesium iodide prepared from 300 mg of magnesium turnings and an equivalent amount of methyl iodide, whilst stirring and cooling. The reaction mixture is refluxed for 2 hours and then worked up in the customary manner. The crude carbinol is subjected to hydrolysis direct, without purification. For this purpose, the compound is dissolved in 10 ml of 66% strength acetic acid and the solution is stirred for 2 hours at 30° C. It is then diluted with water and extracted with ethyl acetate and the extracts are washed until neutral (twice with saturated sodium bicarbonate solution and with water), dried and evaporated in an aspirator vacuum. Chromatography of the crude product over 100 times the amount by weight of silica gel (system: hexane/ethyl acetate, 3:1) gives 18,18-difluoro-17β-hydroxy-17-methyl-androst-4-en-3-one.

EXAMPLE 9

250 mg of 18,18-difluoro-17β-hydroxy-17-methyl-androst-4-en-3-one and 250 mg of 2,3-dicyano-5,6-dichloro-benzoquinone are suspended in 20 ml of absolute benzene and the suspension is refluxed under nitrogen for 16 hours. The cooled reaction mixture is freed from insoluble constituents by filtration and evaporated in an aspirator vacuum, the residue is dissolved in methylene chloride and the solution is filtered through a column charged with 5 g of aluminium oxide, activity II (neutral). The resulting 18,18-difluoro-17$\beta$-hydroxy-17-methyl-androsta-1,4-dien-3-one is purified by recrystallisation from methylene chloride/methanol. IR spectrum: bands at, inter alia, 3600, 1661, 1622 and 1602 cm$^{-1}$.

EXAMPLE 10

250 mg of 18,18-difluoro-17$\beta$-hydroxy-oestr-4-en-3-one are dissolved in 1 ml of pyridine, 1 ml of acetic anhydride is added to the solution and the mixture is left to stand for 15 hours at room temperature. The reaction mixture is then poured into ice water, the mixture is extracted twice with ethyl acetate, washed until neutral, dried and evaporated in an aspirator vacuum. After one crystallisation of the crude product from ether/hexane, pure 18,18-difluoro-17$\beta$-hydroxy-oestr-4-en-3-one acetate of melting point 108°–110° C is obtained.

EXAMPLE 11

280 mg of 18,18-difluoro-oestr-4-ene-3,17-dione, 10 ml of dioxane, 0.5 ml of orthoformic acid ethyl ester and 16 mg of p-toluenesulphonic acid are stirred for 6 hours at room temperature, light being excluded. The reaction mixture is poured into 40 ml of water (containing 4 drops of pyridine), the mixture is extracted twice with ethyl acetate and the organic layer is washed with water and a saturated sodium chloride solution until neutral, dried and evaporated in an aspirator vacuum. The resulting amorphous 3-ethoxy-18,18-difluoro-oestra-3,5-dien-17-one is then dissolved in 6 ml of dioxane and the solution is added dropwise in the course of 20 minutes to a solution, which is saturated with acetylene, of 1.8 g of lithium acetylide-ethylenediamine complex in 18 ml of dioxane, whilst at the same time passing acetylene through the solution. The reaction mixture is then stirred at room temperature for a further 15 minutes and saturated ammonium chloride solution and ethyl acetate are then added with cooling and the organic phase is washed successively with 1 N hydrochloric acid and with a saturated sodium chloride solution, dried and evaporated in an aspirator vacuum. In order to dissolve the resulting yellowish amorphous residue in 5 ml of tetrahydrofuran, 2.5 ml of a 3:7 mixture of concentrated hydrochloric acid and water are then added and the mixture is stirred for 1 hour at room temperature. After adding ethyl acetate, the organic layer is washed with sodium bicarbonate solution and water until neutral (subsequent extraction with ethyl acetate), dried and evaporated in an aspirator vacuum. The residue is chromatographed over 100 times the amount of silica gel, using hexane/ethyl acetate (2:1) as the eluant, to yield 18,18-difluoro-17-hydroxy-19-nor-17$\alpha$-pregn-4-en-20-in-3-one (17$\alpha$-ethinyl-18,18-difluoro-19nor-testosterone), which after recrystallisation from methylene chloride/hexane melts at 244°–252° C. IR spectrum: 3550, 3280, 1670, 1620 and 1055 cm$^{-1}$. NMR spectrum: 2.63 ppm, singlet, (C-21), 5.84 ppm, broad singlet (C-H), 6.13 ppm, triplet, $J_{HF} = 54$ Hz (C-18).

EXAMPLE 12

1 ml of piperidinosulphur trifluoride is added to 350 mg of 20$\beta$-hydroxy-3-oxo-pregn-4-en-18-al acetate at room temperature under an argon atmosphere in a glass flask and the mixture is stirred for 90 minutes at 50° C under argon. The reaction mixture is cooled to 25° C, diluted cautiously with ethyl acetate and poured into ice water. The organic layer is separated and the aqueous layer is additionally extracted with ethyl acetate. The organic extracts are combined, washed with water until neutral, dried over sodium sulphate and evaporated in an aspirator vacuum. The slightly coloured residue is chromatographed over silica gel using hexane/ethyl acetate (3:1) as the solvent. The desired 18,18-difluoro-20$\beta$-hydroxy-pregn-4-en-3-one acetate is obtained from the first fractions and, after recrystallisation from ether/hexane, melts at 188°–190° C. From the subsequent chromatographic fractions, it is possible to recover successively the unconverted starting materials and its analogue which is saponified at the hydroxyl group in the 20-position.

EXAMPLE 13

A solution of 40 mg of potassium hydroxide in 1 ml of water is added to a solution of 50 mg of 18,18-difluoro-20$\beta$-hydroxy-pregn-4-en-3-one acetate in 9 ml of methanol and the mixture is stirred under nitrogen for 3 hours at 45° C. The reaction solution is then evaporated in vacuo to half its volume, diluted with ethyl acetate, washed until neutral, dried and evaporated in an aspirator vacuum. The resulting crude 18,18-difluoro-20$\beta$-hydroxy-pregn-4-en-3-one is homogeneous as shown by thin layer chromatography and can be used without further purification for the oxidation in the next stage.

EXAMPLE 14

A solution of 22 mg of 18,18-difluoro-20$\beta$-hydroxy-pregn-4-en-3-one in 10 ml of acetone is treated with 0.03 ml of a 8 N solution of chromium-VI oxide in dilute sulphuric acid (Jones reagent) at 0° C for 5 minutes. The excess reagent is destroyed with 1 drop of isopropyl alcohol, the reaction mixture is treated with saturated potassium acetate solution, diluted with ethyl acetate and the organic layer is washed with a saturated sodium chloride solution until neutral, dried and evaporated in an aspirator vacuum. The resulting residue is chromatographed over silica gel. Elution with hexane/ethyl acetate (3:1) gives, in the main fraction, 18,18-difluoro-pregn-4-ene-3,20-dione (18,18-difluoroprogesterone), which after recrystallisation from ether/hexane melts at 159°–160° C.

EXAMPLE 15

In a manner analogous to that in Example 12, 1.0 g of 17$\beta$-hydroxy-3-methoxy-oestra-1,3,5(10-trien-18-al acetate is treated with 5 ml of piperidinosulphur trifluoride and worked up. The product obtained is 18,18-difluoro-3-methoxy-oestra-1,3,5(10)-trien-17$\beta$-al acetate, which after recrystallisation from acetone/hexane melts at 124°–125° C.

EXAMPLE 16

In a manner analogous to that in Example 13, a solution of 600 mg of 18,18-difluoro-3-methoxy-oestra-1,3,5(10)-trien-17$\beta$-ol acetate in 20 ml of methanol is saponified with 130 mg of potassium hydroxide in 5 ml of water and worked up. The crude product is dissolved in a mixture of hexane/ethyl acetate (9:1), the solution filtered through silica gel, the solvent evaporated and the residue, which consists virtually only of 18,18-difluoro-3-methoxy-oestra-1,3,5(10-trien-17$\beta$-ol is employed direct in the next operation (the Jones oxidation).

EXAMPLE 17

In a manner analogous to that in Example 14, a solution of 378 mg of crude 18,18-difluoro-3-methoxy-oestra-1,3,5(10)-trien-17β-ol in 15 ml of acetone is oxidised with 0.5 ml of a 8 N solution of chromium-VI oxide in dilute sulphuric acid (Jones reagent) for 20 minutes at 0° C and worked up. The crude product is crystallised direct, without purification by chromatography, from acetone/hexane and 18,18-difluoro-3-methoxy-oestra-1,3,5(10-trien-17-one of melting point 162°–164° C is thus obtained.

EXAMPLE 18

A solution of 300 mg of 18,18-difluoro-3-methoxy-oestra-1,3,5(10)-trien-17-one in 12 ml of dioxane is added dropwise in the course of 30 minutes to a solution, saturated with acetylene, of 1.5 g of lithium acetylide-ethylenediamine complex in 10 ml of dioxane, whilst at the same time passing acetylene through the solution. The reaction mixture is stirred at room temperature for a further 60 minutes and treated, whilst cooling, with saturated ammonium chloride solution and with ethyl acetate. The organic phase is washed successively with 1 N hydrochloric acid and with a saturated sodium chloride solution, dried and evaporated in an aspirator vacuum. The residue is chromatographed over silica gel with a mixture of hexane/ethyl acetate (9:1) as the eluant affording 17α-ethinyl-18,18-difluoro-3-methoxy-oestra-1,3,5(10)-trien-17β-ol, which after recrystallisation from acetone/hexane has a melting point of 167°–168° C.

EXAMPLE 19

A mixture of 400 mg of 17α,20;20,21-bis-methylenedioxy-3,11-dioxo-pregna-1,4-dien-18-al and 1 ml of diethylaminosulphur trifluoride is heated, with stirring, for 3 hours at 55° C in an argon atmosphere. The reaction mixture is cooled to room temperature, ethyl acetate is added cautiously, and the mixture is poured into ice water with stirring. The organic layer is separated, the aqueous layer is extracted with ethyl acetate and the extracts are combined with the main fraction. This solution is washed with water until neutral, dried over sodium sulphate and concentrated in an aspirator vacuum. The residue is chromatographed over silica gel; hexane/ethyl acetate (2:1) is used as the eluant. Amorphous 17α,20;20,21-bis-methylenedioxy-18,18-difluoro-pregna-1,4-diene-3,11-dione, which is homogeneous as shown by chromatography, is isolated from the main fraction; IR spectrum: 1710, 1665, 1625, 1605, 1180, 1135, 1115 and 970 cm$^{-1}$. The corresponding 18,18-difluoroprednisolone (18,18-difluoro-17α,21-dihydroxy-pregna-1,4-diene-3,11,20-trione) is liberated from this derivative in the customary manner using 60% aqueous formic acid.

What we claim is:

1. A compound of the general formula (IB)

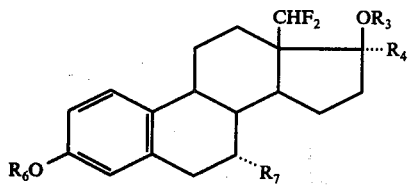

wherein $R_3$ denotes a hydrogen atom or a lower alkyl or lower alkanoyl group, $R_4$ denotes a hydrogen atom or a lower aliphatic hydrocarbon radical, or $R_3$ and $R_4$ conjointly represent a valency bond, $R_6$ denotes a hydrogen atom or a lower alkyl group and $R_7$ denotes a hydrogen atom or the methyl group.

2. A compound of the general formula

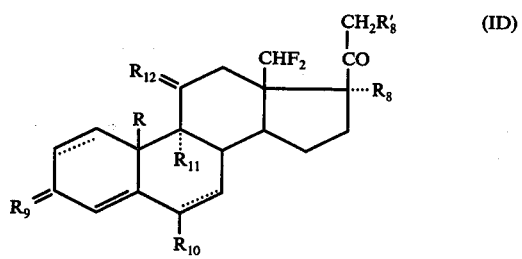

wherein R denotes a hydrogen atom or a methyl group, $R_8$ and $R'_8$ independently of one another each denote a hydrogen atom or an optionally esterified hydroxyl group, $R_9$ denotes an oxo group or denotes a hydrogen atom conjointly with an optionally esterified hydroxyl group, $R_{10}$ denotes a hydrogen atom, the methyl group or a halogen atom, $R_{11}$ denotes a hydrogen atom or a halogen atom and $R_{12}$ denotes two hydrogen atoms or an oxo group or denotes an α-oriented hydrogen atom conjointly with a chlorine atom or a hydroxyl group, it being possible for one double bond to be present in the 6,7-position and, if R represents the methyl group, also in the 1,2-position and/or the 6,7-position.

3. A compound according to claim 2 of the general formula IE

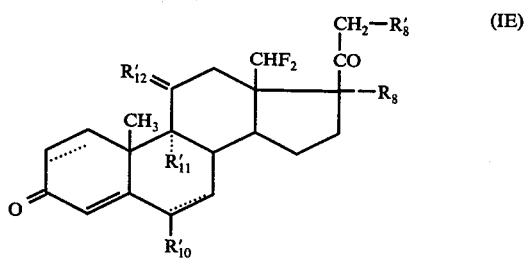

wherein $R_8$ denotes a hydrogen atom or a hydroxyl group which is optionally esterified by a lower alkanecarboxylic acid, $R'_8$ denotes a hydroxyl group which is optionally esterified by a lower alkanecarboxylic acid, $R'_{10}$ denotes a hydrogen atom, a methyl group or a fluorine atom, $R'_{11}$ denotes a hydrogen, chlorine or fluorine atom and $R'_{12}$ denotes an oxo group or denotes an α-oriented hydrogen atom conjointly with a hydroxyl group or, if $R'_{11}$ is a chlorine atom, conjointly with a chlorine atom, it being possible for a double bond to be present in the 1,2-position.

4. A compound of the general formula (IF)

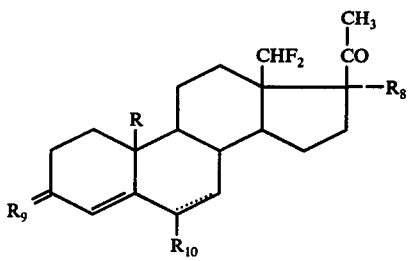

wherein R denotes a hydrogen atom or a methyl group, $R_8$ denotes a hydrogen atom or an optionally esterified hydroxyl group, $R_9$ denotes an oxo group or denotes a hydrogen atom conjointly with an optionally esterified hydroxyl group and $R_{10}$ denotes a hydrogen atom, the methyl group or a halogen atom, it being possible for a double bond to be present in the 6,7-position.

5. A compound according to claim 4 of the formula IF indicated in the said claim, wherein R has the above-mentioned meaning, $R_8$ denotes a hydrogen atom or a hydroxyl group esterified by a lower alkanecarboxylic acid, $R_9$ denotes an oxo group and $R_{10}$ denotes the methyl group or a chlorine atom, a double bond being present in the 6,7-position.

6. A compound selected from the group consisting of 18,18-difluoro-androst-5-ene-3β,17β-diol and its diacetate; 18,18-difluoroandrost-4-ene-3,17-dione; 18,18-difluoro-oestr-4-ene-3,17-dione; 3-ethoxy-18,18-difluoroandrosta-3,5-dien-17-one; 3-ethoxy-18,18-difluoro-17α-methylandrosta-3,5-dien-17β-ol; 3-ethoxy-18,18-difluoro-oestra-3,5-dien-17-one; and 18,18-difluoro-20β-hydroxypregn-4-en-3-one and its acetate.

7. A compound according to claim 1, selected from the group consisting of 18,18-difluoro-3-methoxyoestra-1,3,5(10)-trien-17-one; 18,18-difluoro-3-methoxyoestra-1,3,5(10)-trien-17β-ol and its acetate; and 17α-ethynyl-18,18-difluoro-3-methoxyoestra-1,3,5(10)-trien-17β-ol.

8. A compound according to claim 2, which compound is 18,18-difluoro-17α,21-dihydroxypregna-1,4-diene-3,11,20-trione or its 17,20;20,21-bis-methylenedioxy derivative.

9. A compound according to claim 4, which compound is 18,18-difluoropregn-4-ene-3,20-dione.

10. 18,18-Difluoro-17β-hydroxy-19-nor-17α-pregn-4-en-20-yn-3-one.

* * * * *